(12) United States Patent
Liao et al.

(10) Patent No.: US 10,660,608 B2
(45) Date of Patent: May 26, 2020

(54) MEDICAL IMAGING SYSTEM, SURGICAL GUIDANCE SYSTEM AND MEDICAL IMAGING METHOD

(71) Applicant: TOSHIBA MEDICAL SYSTEMS CORPORATION, Otawara-Shi (JP)

(72) Inventors: Yuhua Liao, Beijing (CN); Guang Li, Beijing (CN)

(73) Assignee: Canon Medical Systems Corporation, Otawara-shi (JP)

( * ) Notice: Subject to any disclaimer, the term of this patent is extended or adjusted under 35 U.S.C. 154(b) by 1042 days.

(21) Appl. No.: 14/809,626

(22) Filed: Jul. 27, 2015

(65) Prior Publication Data
US 2016/0030002 A1 Feb. 4, 2016

(30) Foreign Application Priority Data
Jul. 31, 2014 (CN) .......................... 2014 1 0374101

(51) Int. Cl.
*A61B 8/00* (2006.01)
*A61B 8/08* (2006.01)
(Continued)

(52) U.S. Cl.
CPC .......... *A61B 8/4254* (2013.01); *A61B 5/0035* (2013.01); *A61B 8/4444* (2013.01);
(Continued)

(58) Field of Classification Search
CPC combination set(s) only.
See application file for complete search history.

(56) References Cited

U.S. PATENT DOCUMENTS 8,226,560 B2 * 7/2012 Arai .......................... A61B 8/13
600/443
9,471,981 B2 * 10/2016 Arai .......................... A61B 8/13
(Continued)

FOREIGN PATENT DOCUMENTS

CN         101422378 B     7/2012
CN         103765239 A     4/2014
(Continued)

OTHER PUBLICATIONS

Gao et al., "A Comparison of Two Similarity Measures in Intensity-based Ultrasound Image Registration", Journal of Image and Graphics, 2006, 11 (3).*
(Continued)

*Primary Examiner* — Joel Lamprecht
(74) *Attorney, Agent, or Firm* — Oblon, McClelland, Maier & Neustadt, L.L.P.

(57) ABSTRACT

A medical imaging system according to embodiment includes an ultrasonic probe, positioning circuitry, first mapping relationship estimation circuitry, repositioning circuitry and a display. The first mapping relationship estimation circuitry estimates a first mapping relationship between a position of the ultrasonic probe when a subject is in a first position state and a position of the ultrasonic probe when the subject is in a second position state. The repositioning circuitry determines a target position of a volume image corresponding to the position of the ultrasonic probe in the second position state according to the first mapping relationship and a second mapping relationship between the position of the ultrasonic probe in the first position state and the target position of the volume image of the subject. The display displays the image of the target position obtained from the volume image according to the target position of the volume image.

10 Claims, 6 Drawing Sheets

(51) Int. Cl.
  *A61B 5/00* (2006.01)
  *A61B 5/055* (2006.01)
  *A61B 6/03* (2006.01)

(52) U.S. Cl.
  CPC .......... *A61B 8/5215* (2013.01); *A61B 8/5261* (2013.01); *A61B 5/055* (2013.01); *A61B 6/032* (2013.01); *A61B 6/037* (2013.01); *A61B 8/461* (2013.01)

(56) References Cited

U.S. PATENT DOCUMENTS

| | | |
|---|---|---|
| 2007/0010743 A1 | 1/2007 | Arai |
| 2012/0179040 A1 | 7/2012 | Arai et al. |
| 2012/0184851 A1 | 7/2012 | Arai et al. |
| 2012/0184852 A1 | 7/2012 | Arai et al. |
| 2014/0147027 A1 | 5/2014 | Jain et al. |
| 2014/0148690 A1 | 5/2014 | Kim et al. |

FOREIGN PATENT DOCUMENTS

| | | |
|---|---|---|
| CN | 103839251 A | 6/2014 |
| JP | 2000-238 | 1/2000 |
| JP | 2002-291720 | 10/2002 |
| JP | 2009-22459 | 2/2009 |
| JP | 2011-182933 | 9/2011 |
| WO | WO 2004/098414 A1 | 11/2004 |

OTHER PUBLICATIONS

Combined Chinese Office Action and Search Report dated Oct. 30, 2017 in Chinese Patent Application No. 201410374101.5 (with English translation of Category of Cited Documents).

G. P. Penney, et al., "Registration of Freehand 3D Ultrasound and Magnetic Resonance Liver Images", Medical Image Analysis, 2014, vol. 8, pp. 81-91.

Combined Office Action and Search Report dated Jul. 9, 2018 in Chinese Patent Application No. 201410374101.5.

Japanese Office Action dated Jun. 11, 2019 in Japanese Application No. 2015-146172, citing document AO, therein, 4 pages.

\* cited by examiner

MEDICAL IMAGING SYSTEM, SURGICAL GUIDANCE SYSTEM AND MEDICAL IMAGING METHOD

CROSS-REFERENCE TO RELATED APPLICATIONS

This application is based upon and claims the benefit of priority from Chinese Patent Application No. 201410374101.5, filed on Jul. 31, 2014, the entire contents of which are incorporated herein by reference.

FIELD

Embodiments relate to medical imaging system, surgical guidance system and medical imaging method.

BACKGROUND

A medical imaging technology is known which registers an ultrasonic image obtained in real time with other pre-obtained medical image such as a Magnetic Resonance (MR) image or a Computed Tomography (CT) image to obtain the mapping relationship between the position of an ultrasonic probe and a target position in the pre-obtained medical image and presents the other medical image as a reference image according to the position of the ultrasonic probe while imaging an imaged object through an ultrasonic imaging device using the mapping relationship.

In the foregoing technology, the mapping relationship can be obtained in the following way: after a certain reference part of the imaged object is imaged by the ultrasonic probe, the ultrasonic image of the reference part is registered with the image of a corresponding position, for example, a manually selected position, in the CT or MR image of the imaged object.

However, the mapping relationship between the position of an ultrasonic probe and a target position in a pre-obtained medical image is effective only when the position of an imaged object is kept unchanged. The foregoing process involving image selection and registration process needs to be repeated to update the mapping relation once the position of the imaged object is changed, for example, when the body of an imaged patient is moved. The operation of re-determining the mapping relationship is relatively tedious and time-consuming. Especially in the application scenario of an interventional surgery which needs a relatively long operation process during which the imaged object may be moved repeatedly, the processing load is increased and more time is consumed.

BRIEF DESCRIPTION OF THE DRAWINGS

Embodiments will be better understood with reference to the following description when taken in conjunction with accompanying drawings in which identical or like reference signs designate identical or like components. The accompanying drawings, together with the detailed description below, are incorporated into and form a part of the specification and serve to illustrate, by way of example, preferred embodiments and to explain the principle and advantages of the embodiments. In the accompanying drawings.

DETAILED DESCRIPTION

A medical imaging system according to an embodiment includes an ultrasonic probe, positioning circuitry, first mapping relationship estimation circuitry, repositioning circuitry and a display. The ultrasonic probe is configured to transmit and receive ultrasonic waves. The positioning circuitry is attached to the ultrasonic probe to detect a position of the ultrasonic probe. The first mapping relationship estimation circuitry is configured to record the position of the ultrasonic probe when a subject is in a first position state and the position of the ultrasonic probe when the subject is in a second position state and estimate a first mapping relationship between the position of the ultrasonic probe in the first position state and the position of the ultrasonic probe in the second position state. The repositioning circuitry is configured to determine a target position of a volume image corresponding to the position of the ultrasonic probe in the second position state according to the first mapping relationship and a second mapping relationship between the position of the ultrasonic probe in the first position state and the target position of the volume image of the subject. The display is configured to obtain an image of the target position from the volume image according to the target position of the volume image determined by the repositioning circuitry and display the obtained image.

The following presents a simplified summary of embodiments to provide a basic understanding of some aspects of embodiments. It should be appreciated that the simplified summary, which is not the exhaustive overview of embodiments, is not intended to identify the key or critical parts of embodiments or limit the scope of embodiments, but merely to present some concepts in a simplified form as a prelude to the more detailed description that is discussed later.

It should be noted that the term 'position', as used herein, of a certain object (e.g. an imaged object, an ultrasonic probe) should be appreciated as including the coordinate position (e.g. the coordinate of a reference point such as the center of mass of the object) and the orientation (e.g. the direction angle of the reference axis of the object and the rotation angle around the reference axis) of the object unless otherwise specified.

In accordance with an aspect of embodiments, a medical imaging system is provided which comprises: an ultrasonic probe configured to transmit and receive ultrasonic waves, positioning circuitry attached to the ultrasonic probe to detect a position of the ultrasonic probe, first mapping relationship estimation circuitry configured to record the position of the ultrasonic probe when a subject is in a first position state and the position of the ultrasonic probe when the subject is in a second position state and estimate a first mapping relationship between the position of the ultrasonic probe in the first position state and the position of the ultrasonic probe in the second position state, repositioning circuitry configured to determine a target position of a volume image corresponding to the position of the ultrasonic probe in the second position state according to the first mapping relationship and a second mapping relationship between the position of the ultrasonic probe in the first position state and the target position of the volume image of the subject, and a display configured to obtain an image of the target position from the volume image according to the target position of the volume image determined by the repositioning circuitry and display the obtained image.

According to an embodiment, a medical imaging system is provided which comprises: an ultrasonic imaging subsystem equipped with an ultrasonic probe; a positioning subsystem configured to determine the position of the ultrasonic probe; a first mapping relationship estimation unit configured to estimate a first mapping relationship according to the position of the ultrasonic probe imaging the same reference part of the subject when the subject is in a first position state and when the subject is in a second position state, wherein the first mapping relationship maps the second position of the ultrasonic probe to the first position so that the ultrasonic probe at the first position in the first state images the same part of the subject with the ultrasonic probe at the second position in the second position state; a repositioning unit configured to determine the target position of the volume image corresponding to the position of the ultrasonic probe in the second position state according to the first mapping relationship and a second mapping relationship between the position of the ultrasonic probe in the first position state and the position of the volume image; and a display subsystem configured to obtain an image of the target position according to the volume image and display the obtained image.

In accordance with another aspect of embodiments, a surgical guidance system is provided which comprises the medical imaging system according to the embodiment.

In accordance with still another aspect of embodiments, a medical imaging method is provided, which comprises the following steps of: transmitting and receiving ultrasonic waves using an ultrasonic probe, detecting the position of the ultrasonic probe, recording the position of the ultrasonic probe when the subject is in a first position state and the position of the ultrasonic probe when the subject is in a second position state and estimating a first mapping relationship according to the position of the ultrasonic probe in the first position state and the position of the ultrasonic probe in the second position state; obtaining a volume image and estimating the relationship between the position of the ultrasonic probe in the first position state and the position of the volume image as a second mapping relationship; determining the target position of the volume image corresponding to the position of the ultrasonic probe in the second position state according to the first and the second mapping relationship; and obtaining the image of the target position according to the volume image and displaying the obtained image.

According to an embodiment, a medical imaging method using an ultrasonic imaging system equipped with an ultrasonic probe is provided, comprising the following steps of: detecting a position of the ultrasonic probe configured to transmit and receive ultrasonic waves, recording the position of the ultrasonic probe when a subject is in a first position state and the position of the ultrasonic probe when the subject is in a second position state, estimating a first mapping relationship between the position of the ultrasonic probe in the first position state and the position of the ultrasonic probe in the second position state, determining a target position of a volume image corresponding to the position of the ultrasonic probe in the second position state according to the first mapping relationship and a second mapping relationship between the position of the ultrasonic probe in the first position state and the target position of the volume image of the subject, obtaining the image of the target position from the volume image according to the target position of the volume image determined by the repositioning circuitry; and displaying the obtained image.

In accordance with yet another aspect of embodiments, a program product is provided in which machine-readable instruction codes are stored. When read and executed by a computer, the instruction codes enable the computer to execute the medical imaging method according to the foregoing embodiments.

In accordance with yet still another aspect of embodiments, a storage medium is provided carrying the program product in which the foregoing machine-readable instruction codes are stored.

According to embodiments, a processing load is reduced when the position of an imaged object is changed.

Embodiments are described below with reference to accompanying drawings. In the embodiments, the elements and features described in an accompanying drawing or implementation mode may be combined with those described in one or more other accompanying drawings or implementation modes. It should be noted that for the sake of clarity, the components and processing that are unrelated to the embodiments but well known to those of ordinary skill in the art are omitted in accompanying drawings and description.

Figure 1:
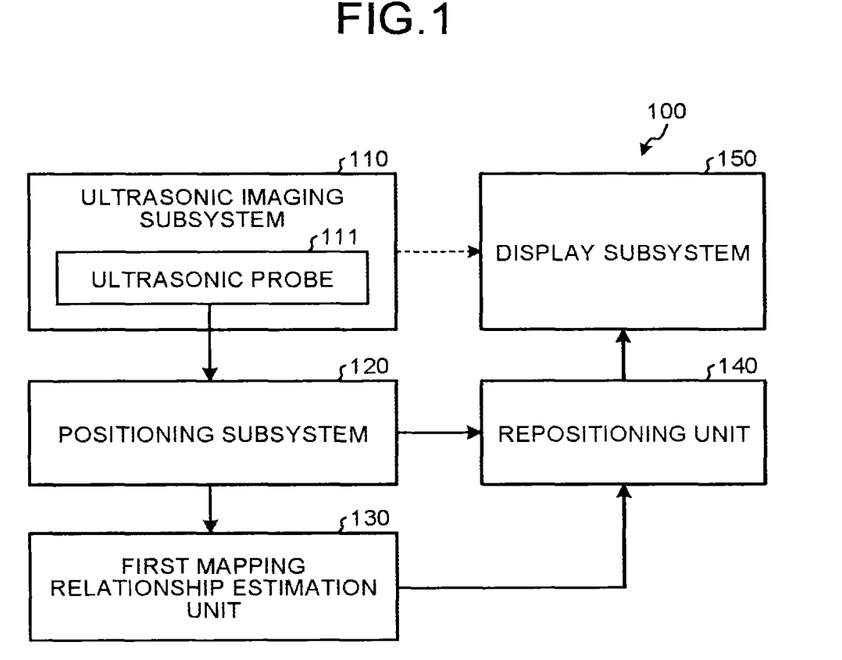
FIG. 1 is a block diagram exemplifying the configuration of a medical imaging system according to an embodiment.

As shown in FIG. 1, according to an embodiment, a medical imaging system 100 comprises an ultrasonic imaging subsystem 110, a positioning subsystem 120, a first mapping relationship estimation unit 130, a repositioning unit 140 and a display subsystem 150. The positioning subsystem 120 is an example of positioning circuitry. The first mapping relationship estimation unit 130 is an example of first mapping relationship estimation circuitry. The repositioning unit 140 is an example of repositioning circuitry. The display subsystem 150 is an example of a display.

The ultrasonic imaging subsystem 110 comprises an ultrasonic probe 111. As is known in the art, the ultrasonic probe 111 can be placed on a target part of an imaged object to transmit and receive ultrasonic waves. The ultrasonic imaging subsystem 110 can generate an ultrasonic image of the target part according to a signal obtained by the ultrasonic probe 111. The ultrasonic imaging subsystem 110 may include an ultrasonic imaging system for obtaining a two-dimensional image, a three-dimensional image or a dynamic image. The specific configuration of the ultrasonic imaging subsystem 110 and the other components the ultrasonic imaging subsystem 110 may comprise are well known in the art and are therefore not presented or described here in detail.

The positioning subsystem 120 is configured to determine the position (including coordinate position and orientation) of the ultrasonic probe 111. The positioning subsystem 120 may include, for example, a magnetic positioning system which may include a magnetic positioning sensor fixed on the ultrasonic probe 111. However, the positioning subsystem 120 is not limited to a magnetic positioning system and may employ other positioning methods, including optical positioning, ultrasonic positioning or the combination thereof.

The first mapping relationship estimation unit 130 is configured to estimate the following mapping relationship: a mapping relationship which is capable of mapping a second position of the ultrasonic probe 111 to a first position when the subject is moved, that is, the subject is changed from a first position state to a second position state, wherein the part imaged by the ultrasonic probe 111 at the second position for the subject in the second position state is the same as that imaged by the ultrasonic probe 111 at the first position for the subject in the first position state. In other words, when the position of the subject is changed, by means of the mapping relationship, the position of the ultrasonic probe 111 for imaging the subject in the second position state can be corresponded to that of the ultrasonic probe 111 for imaging the same part of the subject in the first position state. The mapping relationship is hereinafter referred to a first mapping relationship to be distinguished from the others. In specific applications, the mapping relationship may have the form of a transformation matrix.

The first mapping relationship estimation unit 130 may estimate the first mapping relationship according to the position of the ultrasonic probe 111 imaging the same reference part of the subject when the subject is in the first position state and when the subject is in the second position state.

Figure 3:
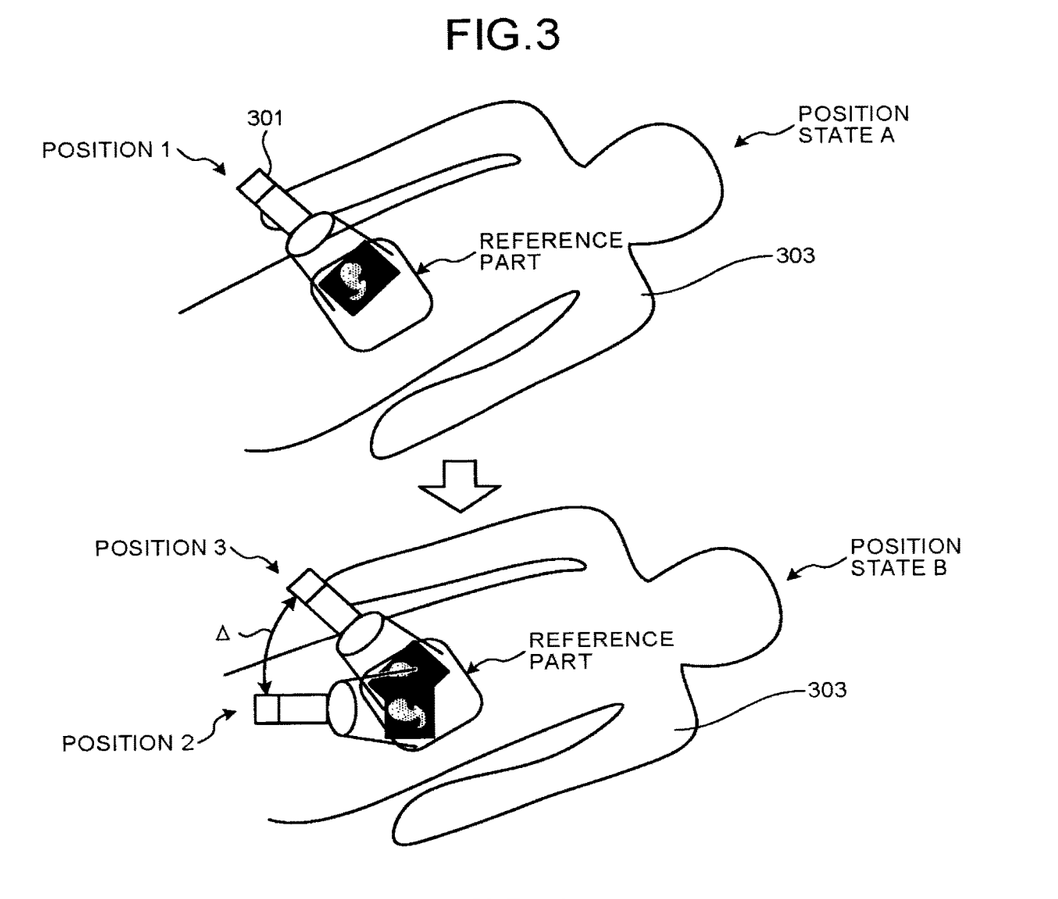
FIG. 3 is a schematic diagram illustrating a medical imaging process conducted by a medical imaging system according to an embodiment.

A more detailed description is given below with reference to the schematic diagram of FIG. 3. As shown in FIG. 3, when a subject 303 is in a position state A, for example, when the operator places an ultrasonic probe 301 on a reference part of the subject 303, the system can record the current position of the ultrasonic probe 301 determined by the positioning subsystem 120, for example, the position 1 shown in FIG. 3. When the subject 303 is moved to enter into a position state B, the operator may place the ultrasonic probe 301 on the same reference part of the subject 303, and the system records the current position of the ultrasonic probe 301 determined by the positioning subsystem, for example, the position 2 shown in FIG. 3. The first mapping relationship estimation unit 130 can determine the first mapping relationship according to the relative position relationship between the position 2 and the position 1. In the following description, the position state A may be named a first position state, and the position state B may be named a second position state.

It should be noted that the difference between the first and the second position state of the subject may include a component of the translation of a coordinate position and a component of the rotation of an azimuth angle.

Besides, the reference part may be a part of an imaged object operated for imaging or a certain part specifically selected for estimating the above-described mapping relationship.

Return to refer to FIG. 1, a repositioning unit 140 is configured to determine the target position of a volume image corresponding to the position of the ultrasonic probe 111 in the second position state according to the first mapping relationship estimated by the first mapping relationship estimation unit 130 and a second mapping relationship. The volume image refers to a medical image, for example, a CT image, an MR image, a PET (Positron Emission Tomography) image, of the subject obtained in advance, and by designating a target position (may include coordinates and captured angle), an image for presentation can be obtained according to the volume image. The second mapping relationship is a pre-obtained mapping relationship between the position of the ultrasonic probe 111 in the first position state and the position of the volume image, that is, a mapping relationship for making the position of the ultrasonic probe 111 corresponding to the target position in the volume image in the first position state. In other words, the target position in the volume image can be determined based on the second mapping relationship according to the position of the ultrasonic probe if the first position state of the subject is kept unchanged.

For example, the second mapping relationship may be obtained in the following way: the ultrasonic image of the subject is registered with the image of a corresponding target position obtained according to the volume image when the subject is in the first position state so as to make the target position in the volume image corresponding to the position of the ultrasonic probe. Specifically, for example, the operator may place the ultrasonic probe on a certain part of the subject to obtain an ultrasonic image and then select a target position (for example, select a coordinate and a captured angle in the volume image according to the part where the ultrasonic probe is placed and the orientation of the placed ultrasonic probe) of the volume image to obtain, according to the volume image, an image substantially corresponding to the ultrasonic image and then perform image registration. During the image registration process, for example, feature points corresponding to the same position of the subject may be designated in the ultrasonic image and a corresponding image obtained from the volume image for the registration.

As stated above, the ultrasonic image may include a two-dimensional image and a three-dimensional image, and the ultrasonic image may be registered with the volume image using a corresponding registration method. For example, the following documents may be referred to: Penney G P, 'Registration of freehand 3D ultrasound and magnetic resonance liver images', Med Image Anal. 2004 March; 8(1): 81-91; Antoine Leroy, 'Rigid Registration of Freehand 3D Ultrasound and CT-Scan Kidney Images', Medical Image Computing and Computer-Assisted Intervention MICCAI 2004 Lecture Notes in Computer Science Volume 3216, 2004, pp 837-844.

Specifically, in the case where the mapping relationship has the form of a transformation matrix, assuming that $P_{prob}$ represents the position of the ultrasonic probe, $P_{target}$ represents the target position in the volume image, $T_{prob\text{-}prob}$ represents the first mapping relationship and $T_{prob\text{-}target}$ represents the second mapping relationship, then the target position can be determined using the following formula when the subject is in the first position state:

$$P_{target} = T_{prob\text{-}target} * P_{prob}$$

If the subject is changed from the first position state to the second position state, then the target position can be determined using the following formula:

$$P_{target} = T_{prob\text{-}target} * T_{prob\text{-}prob} * P_{prob}$$

The display subsystem 150 is configured to obtain, according to the volume image, the image of the target position determined by the repositioning unit 140 and display the obtained image.

According to an embodiment, the display subsystem 150 is configured to synchronously display the image obtained according to the volume image and the ultrasonic image obtained by the ultrasonic imaging subsystem 110. Thus, an ultrasonic image of the subject is formed while other pre-obtained medical image is presented as a reference image.

With the configuration described above, when the position of the subject is changed, the presentation of a reference image can be continued merely by determining the first mapping relationship (Tprob-prob) between the position of the ultrasonic probe in the second position state and the position of the ultrasonic probe in the first position state with a relatively simple operation, requiring no determination (that is, updating) of the second mapping relationship (Tprob-target) between the position of the ultrasonic probe and the target position in the volume image.

For the operator, information for estimating the first mapping relationship can be obtained merely by conducting the following simple operation: placing the ultrasonic probe at a position where the ultrasonic probe images a reference part of the subject when the subject is in the first position state and recording the current position of the ultrasonic probe, and placing the ultrasonic probe again at a position where the ultrasonic probe images the reference part when the subject is moved to enter into the second position state and recording the current position of the ultrasonic probe. Thus, according to the foregoing embodiments, the processing load caused by updating the mapping relationship when the position of the subject is changed can be reduced.

In addition, in the case where the position of the subject is changed repeatedly, the first mapping relationship can be estimated according to the position information obtained in the current position state and that obtained in the first position state (initial position state) without using the position information and the mapping relationship obtained in an intermediate position state, every time the position of the subject is changed, thereby preventing the accumulation of errors.

In the foregoing embodiments, the first mapping relationship estimation unit 130 estimates the first mapping relationship according to the position of the ultrasonic probe imaging the same reference part of the subject when the subject is in the first position state and when the subject is in the second position state. It is ideal that the ultrasonic probe is placed at the same relative position with respect to the subject every time. However, if, for example, the relative position of the ultrasonic probe with respect to the subject is changed due to the deviation in the manual operation of the operator when the ultrasonic probe is placed two times as described above, then the target position determined by the repositioning unit 140 based on the first mapping relationship estimated in this way is deviated, which may result in that the imaged part of the reference image obtained from the volume image according to the target position of the volume image, although substantially identical to the part currently imaged by the ultrasonic probe, may be horizontally shifted and/or rotationally deviated.

Refer to the example shown in FIG. 3 again, assuming that the ultrasonic probe is placed at the position 1 in the position state A and at the position 2 in the position state B and that the first mapping relationship is estimated according to the positions 1 and 2. As shown in FIG. 3, the deviation in manual operations causes a deviation Δ between the relative position of the ultrasonic probe at the position 1 with respect to the subject in the position state A and that of the ultrasonic probe at the position 2 with respect to the subject in the position state B. The deviation between an actual position (position 2) and an ideal position (3) may include the following components: the translation deviation of the ultrasonic probe, the deviation of the axial direction angle of the ultrasonic probe and the deviation of the rotation angle of the ultrasonic probe around the axis of the ultrasonic probe.

Therefore, what is described below is an object of the embodiment for relieving the influence caused by manual operation to increase the accuracy of the target position in the determined volume image.

Figure 2:
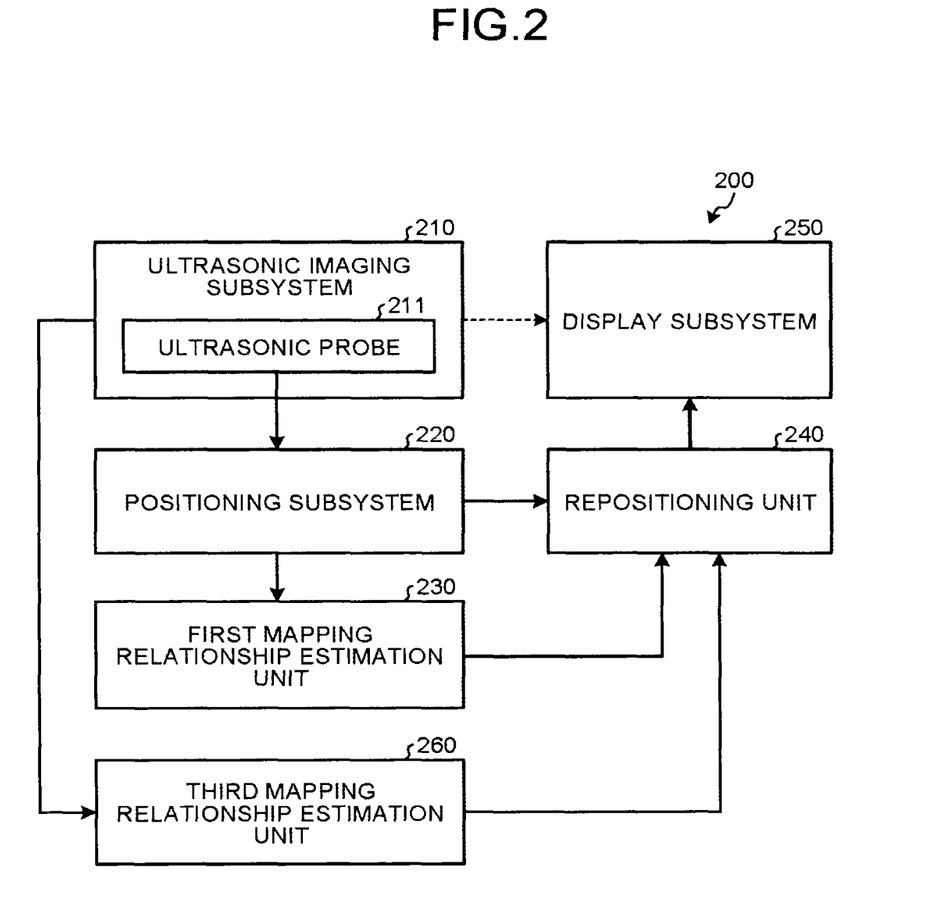
FIG. 2 is a block diagram exemplifying the configuration of a medical imaging system according to another embodiment.

As shown in FIG. 2, according to another embodiment, a medical imaging system 200 comprises an ultrasonic imaging subsystem 210 (comprising an ultrasonic probe 211), a positioning subsystem 220, a first mapping relationship estimation unit 230, a repositioning unit 240, a display subsystem 250 and a third mapping relationship estimation unit 260. The positioning subsystem 220 is an example of the positioning circuitry. The first mapping relationship estimation unit 230 is an example of the first mapping relationship estimation circuitry. The repositioning unit 240 is an example of the repositioning circuitry. The display subsystem 250 is an example of the display. The third mapping relationship estimation unit 260 is an example of third mapping relationship estimation circuitry.

The ultrasonic imaging subsystem 210, the positioning subsystem 220, the first mapping relationship estimation unit 230 and the display subsystem 250 are similar in configuration to the ultrasonic imaging subsystem 110, the positioning subsystem 120, the first mapping relationship estimation unit 130 and the display subsystem 150 described above with reference to FIG. 1.

The third mapping relationship estimation unit 260 is configured to estimate a third mapping relationship, wherein the combination of the third mapping relationship with the first mapping relationship (e.g. in the case where a mapping relationship is represented by a transformation matrix, the product of transformation matrixes of the first and the third mapping relationship may be taken as the combination) maps a third position of the ultrasonic probe 211 to the first position so that the image formed by the ultrasonic probe at the first position for the subject in the first position state is the same as that imaged by the ultrasonic probe at the third position for the subject in the second position state. In other words, the third mapping relationship is used to counteract the difference, for example, the deviation Δ shown in FIG. 3, of the relative position of the ultrasonic probe with respect to the subject caused by the deviation in the mutual operation of the operator. That is, the third mapping relationship is used to correct the deviation Δ.

The third mapping relationship estimation unit 260 estimates a third mapping relationship according to the registration deviation between the ultrasonic images formed by imaging a reference part of the subject when the subject is in the first position state and when the subject is in the second position state. The registration deviation between ultrasonic images can be determined using a variety of existing methods. For instance, the following documents may be referred to: Gao Shuang, 'A Comparison of Two Similarity Measures in Intensity-based Ultrasound Image Registration', JOURNAL OF IMAGE AND GRAPHICS, 2006, 11 (3).

According to an embodiment, the local variance of the brightness value of an ultrasonic image may be calculated, and the foregoing registration deviation can be determined based on a variogram in which the local variance is mapped to an image. That is, the variogram of taken ultrasonic images is compared with the variogram of a registered object, and the position where the offset is minimal is determined as a registration deviation. Further, as another method, high-frequency images of extracted image-based high-frequency areas highly contributive to registration are compared with each other to perform registration, thereby further improving processing efficiency.

The estimation of the third mapping relationship based on an ultrasonic image obtained by imaging the reference part in the first position state and an ultrasonic image obtained by imaging the reference part in the second position state has the following advantages: as the images to be compared are both ultrasonic images, the image difference caused by different imaging methods is avoided, thus making it possible to perform registration without, for example, manually selecting feature points, besides, as the images to be compared substantially aim at the same part, there is no need to search or manually select the image areas to be compared. Therefore, the foregoing registration deviation can be determined automatically without the intervention of the operator, thus reducing the operation load of the operator.

Similar to the embodiment described with reference to FIG. 1, the medical imaging system of this embodiment described with reference to FIG. 2 can obtain information for estimating the first and the third mapping relationship by carrying out the following simple operation when the position of the subject is changed: placing the ultrasonic probe at a position where a reference part of the subject is imaged to image the reference part when the subject is in the first position state and recording the current position of the ultrasonic probe and the obtained ultrasonic image, and placing the ultrasonic probe at the position where the reference part of the subject is imaged again to image the reference part when the subject is moved to a second position state and recording the current position of the ultrasonic probe. In other words, compared with the embodiments described with reference to FIG. 1, only a processing of forming an ultrasonic image of the reference part is increased in the present embodiment, which substantially causes no additional actual operation load for the operator.

Further, according to an embodiment, a part on which the influence of the respiratory movement of the subject is below a predetermined level, for example, the neck or the hypogastrium of the subject, may be selected as the reference part to reduce the influence of the respiratory movement of the subject on the foregoing registration deviation to be beneficial to make the third mapping relationship to be estimated more accurately according to the foregoing registration deviation. However, a present embodiment is not limited to the reference part selected in the way described above, for example, if the reference part is severely influenced by respiratory movement, the third mapping relationship may be estimated based on the ultrasonic images obtained in a specific stage (e.g. the end of expiration or inspiration) of a respiratory cycle, thereby reducing the influence caused by respiratory movement.

Additionally, as stated above, the ultrasonic image obtained by the ultrasonic imaging subsystem according to embodiments may include a two-dimensional image, a three-dimensional image or a dynamic image. For two-dimensional images and three-dimensional images, the registration deviation between ultrasonic images can be determined using methods specific to two-dimensional images and three-dimensional images. For example, the following documents may be referred to: Foroughi P, 'Elastic registration of 3D ultrasound images', Med Image Comput Comput Assist Interv. 2005; 8(Pt 1): 83-90). Further, for dynamic images, the foregoing registration variation can be determined based on frames of the images. It should be noted that the registration deviation may include a translation component and a rotation component.

correspondingly, the repositioning unit 240 is configured to determine the target position of a volume image corresponding to the position of the ultrasonic probe in the second position state according to the first mapping relationship estimated by the first mapping relationship estimation unit 230, the pre-obtained second mapping relationship between the position of the ultrasonic probe 211 in the first position state and the position in the volume image and the third mapping relationship estimated by the third mapping relationship estimation unit 260.

Specifically, in the case where the mapping relationship has the form of a transformation matrix, assuming that Pprob represents the position of the ultrasonic probe, $P_{target}$ represents the target position in the volume image, $T_{prob-prob}$ represents the first mapping relationship, $T_{prob-target}$ represents the second mapping relationship and $T_{ultra-ultra}$ represents the third mapping relationship, then the target position can be determined using the following formula when the subject is changed from the first position state to the second position state:

$$P_{target}=T_{prob-target}*T_{ultra-ultra}*T_{prob-prob}*P_{prob}$$

By using the medical imaging system according to the present embodiment, the influence caused by the error in the position of the ultrasonic probe placed by the operator is reduced to determine the target position of an image corresponding to the position of the ultrasonic probe more accurately. Moreover, no actual operation load is increased for the operator.

Figure 4:
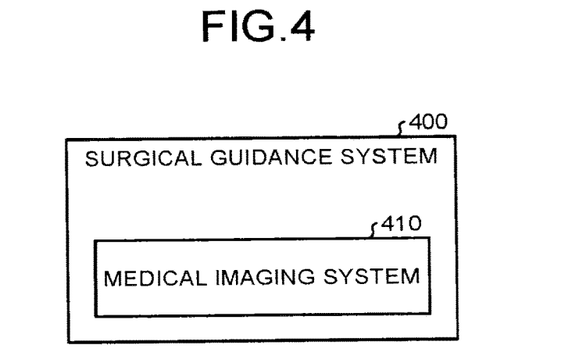
FIG. 4 is a block diagram exemplifying the configuration of a surgical guidance system according to an embodiment.

The medical imaging system according to embodiments of the present embodiment can be applied to a surgical guidance system. As shown in FIG. 4, a surgical guidance system 400 according to an embodiment of the present embodiment includes a medical imaging system 410. The surgical guidance system 400 may include, for example, a guidance system for an interventional surgery.

The medical imaging system 410 may have the above-described configuration according to embodiments of the present embodiment and can be used to image before an operation, during an operation (especially for an interventional operation) or after an operation to improve the safety of the operation and to conduct an effect assessment.

The medical imaging system 410 may present other medical image, for example, a CT image, an MR image or a PET image corresponding to the imaging position of an ultrasonic image while providing the ultrasonic image in real time, thereby providing more reference information.

Moreover, by updating a mapping relationship for repositioning the target position with a relatively simple operation when the operated object is moved during the operation, the operation load of the operator is reduced and the surgery time is reduced.

It is apparent that some processing or methods are also disclosed in the foregoing description on the medical imaging system in embodiments. These methods are summarized hereinafter without repeatedly describing the details discussed above.

Figure 5:
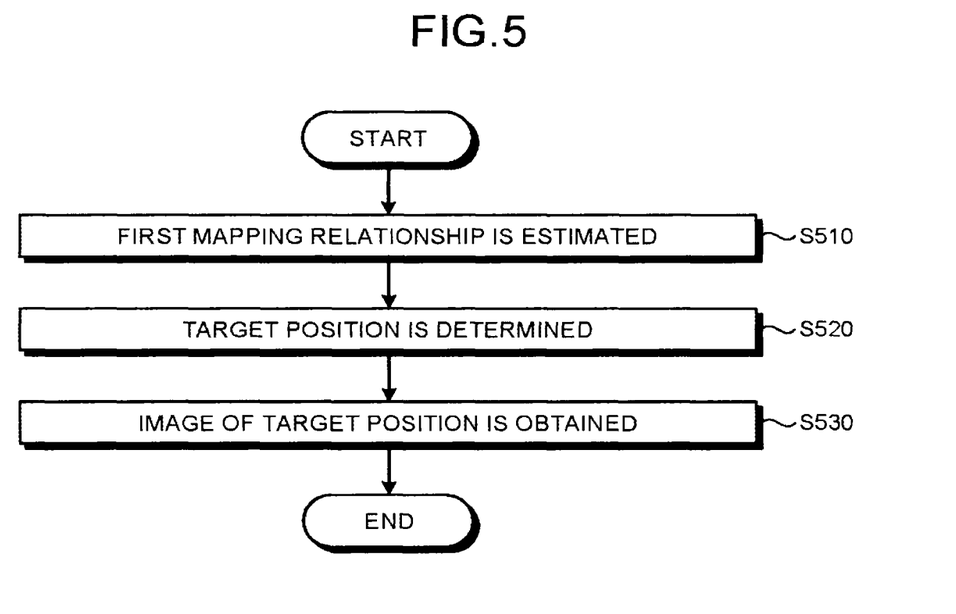
FIG. 5 is a flowchart exemplifying the process of a medical imaging method according to an embodiment.

FIG. 5 shows a medical imaging method using an ultrasonic imaging system comprising an ultrasonic probe according to an embodiment.

In Step S510, a first mapping relationship is estimated according to the positions of an ultrasonic probe imaging the same reference part of a subject when the subject is in a first position state and when the subject is in a second position state by the first mapping relationship estimation unit 130. The first mapping relationship maps a second position of the ultrasonic probe to a first position so that the ultrasonic probe at the first position in the first position state and the ultrasonic probe at the second position in the second position state perform imaging for the same part of the subject.

According to a specific embodiment, the position of the ultrasonic probe is determined using a magnetic positioning sensor fixed on the ultrasonic probe. However, the present embodiment is not limited to this, other positioning methods, including optical positioning or ultrasonic positioning, are also applicable.

In Step S520, the target position of a volume image corresponding to the position of the ultrasonic probe in the second position state is determined according to the first mapping relationship and a second mapping relationship between the position of the ultrasonic probe in the first position state and the position in the volume image by the repositioning unit 140.

The second mapping relationship may be obtained by, for example, registering the ultrasonic image of the subject in the first position state with an image of a corresponding position obtained according to a volume image. The ultrasonic image may include a two-dimensional image, a three-dimensional image or a dynamic image. The volume image may include a CT image, an MR image or a PET image.

In Step S530, the image of the target position is obtained according to the volume image and the obtained image is displayed by the display subsystem.

According to an embodiment, the image obtained according to the volume image (serving as a reference image) and the ultrasonic image obtained by the ultrasonic imaging subsystem may be displayed synchronously.

Figure 6:
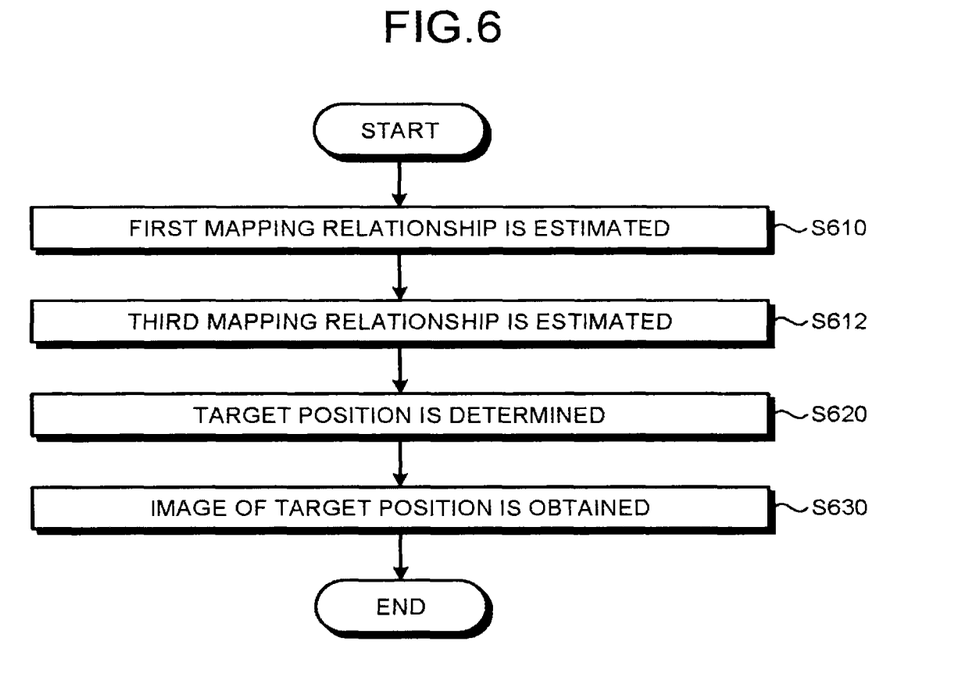
FIG. 6 is a flowchart exemplifying the process of a medical imaging method according to another embodiment.

In the medical imaging method disclosed in another embodiment and shown in FIG. 6, Steps S610 and S630 are similar to Steps S510 and S530 described above with reference to FIG. 5, respectively.

In Step S612, a third mapping relationship is estimated according to the registration deviation between the ultrasonic images formed by imaging a reference part of a subject when the subject is in the first position state and when the subject is in the second position state by the third mapping relationship estimation unit 260.

The combination (e.g. the product of transformation matrixes) of the third mapping relationship with the first mapping relationship maps a third position of the ultrasonic probe to the first position so that the image formed by the ultrasonic probe at the first position for the subject in the first position state is the same as that imaged by the ultrasonic probe at the third position for the subject in the second position state.

According to an embodiment, a registration deviation for estimating the third mapping relationship is determined based on the variogram of ultrasonic images.

For a two-dimensional ultrasonic image and a three-dimensional ultrasonic image, the foregoing registration deviation can be obtained using a corresponding image processing method.

According to an embodiment, the reference part can be selected from the parts of the subject on which the influence of respiratory movement is below a predetermined level. However, the present embodiment is not limited this, for example, the third mapping relationship may be estimated based on the ultrasonic images obtained in a specific stage of a respiratory cycle, thereby reducing the influence caused by respiratory movement.

In Step S620, the target position of a volume image corresponding to the position of the ultrasonic probe in the second position state is determined according to the first mapping relationship, the second mapping relationship and the third mapping relationship (e.g. the product of transformation matrix) by the repositioning unit 240.

As an example, each step of the above-described medical imaging and each module and/or unit of the above-described medical imaging system may be implemented as software, firmware, hardware or the combination thereof. In the case where the steps and the modules and/or units are achieved through software or firmware, a software program for realizing the above-described method is installed in a computer having a specific hardware structure (e.g. the general computer 700 shown in FIG. 7) from a storage medium or network, and the computer, when installed with various program, is capable of executing various functions.

Figure 7:
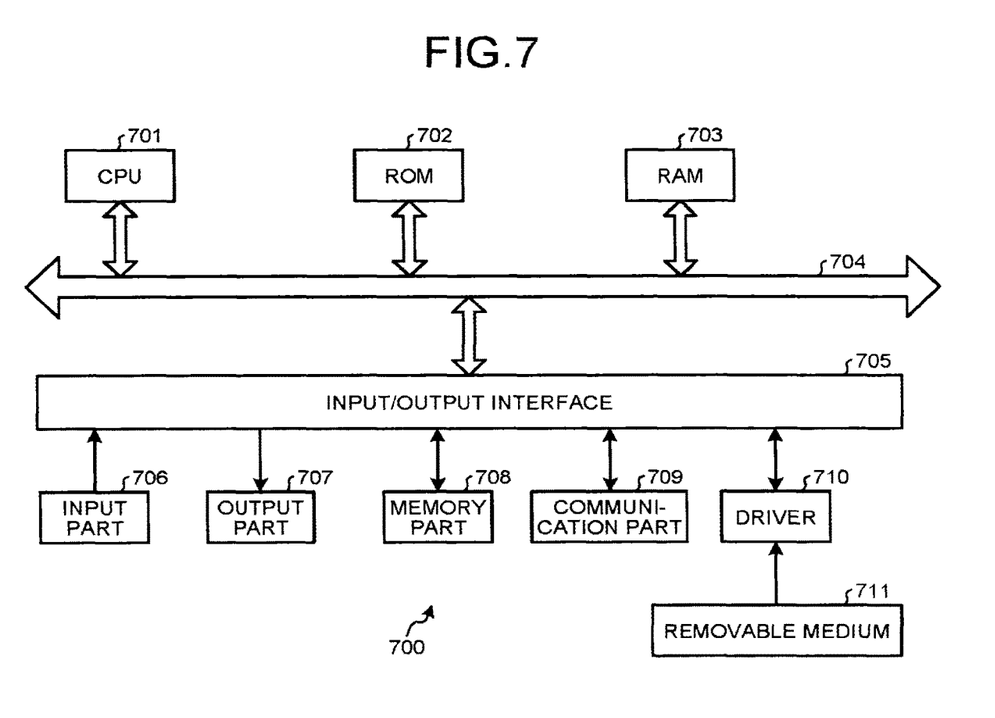
FIG. 7 is a block diagram illustrating an exemplary structure of a computer for realizing the method and the device of embodiments.

In FIG. 7, a central processing unit (namely, CPU) 701 executes various processing according to a program stored in a read-only memory (ROM) 702 or a program loaded to a random access memory (RAM) 703 from a memory part 708. The data needed for the various processing of the CPU 701 may be stored in the RAM 703 as needed. The CPU 701, the ROM 702 and the RAM 703 are connected with each other via a bus line 704. An input/output interface 705 is also connected with the bus 704.

The following components are linked with the input/output interface 705: an input part 706 (including keyboard, mouse and the like), an output part 707 (including displays such as cathode ray tube (CRT), liquid crystal display (LCD) and loudspeaker), the memory part 708 (including hard disk and the like) and a communication part 709 (including a network interface card such as LAN card and modem). The communication part 709 carries out a communication processing via a network such as the Internet. If needed, a driver 710 may also be linked with the input/output interface 705. If needed, a removable medium 711, for example, a magnetic disc, an optical disc, a magnetic optical disc, a semiconductor memory and the like, may be installed in the driver 710 to read a computer program therefrom and install the read computer program in the memory part 708 as needed.

In the case where the foregoing series of processing is achieved through software, programs forming the software are installed from a network such as the Internet or a storage medium such as the removable medium 711.

It should be appreciated by those skilled in this art that the storage medium is not limited to the removable mediums 711 shown in FIG. 7 in which programs are stored and which are distributed separated from the apparatus to provide the programs for users. The removable medium 711 may be, for example, a magnetic disc (including floppy disc (registered trademark)), a compact disc (including compact disc read-only memory (CD-ROM) and digital video disk (DVD)), a magnetic optical disc (including mini disc (MD) (registered trademark)), and a semiconductor memory. Alternatively, the storage mediums may be the hard discs included in ROM 702 and the memory part 708, and programs are stored in the storage medium and can be distributed to users along with the storage medium.

An embodiment further provides a program product in which computer-readable instruction codes are stored. The aforementioned image processing method can be implemented when the instruction codes are read and executed by a machine.

Accordingly, a storage medium for storing the program product in which computer-readable instruction codes are stored is also included in the embodiment. The storage medium includes but is not limited to a soft disc, an optical disc, a magnetic optical disc, a memory card, a memory stick and the like.

In the foregoing description on the specific embodiments, the features described and/or shown for an implementation mode may be used in one or more other implementation modes in the same or like way or combined with those of the other implementation modes, or replace those of the other implementation modes.

It should be emphasized that the terms 'comprise/include', as used herein, means the existence of a feature, element, step or component in a way not exclusive of the existence or addition of one or more other features, elements, steps or components.

In the above-described embodiments and examples, each step and/or unit is represented with a reference sign consisting of figures. It should be understood by those of ordinary skill of the art that the reference signs are merely intended to facilitate description and drawing but are not to be construed as a limitation on an order or any other aspect.

Furthermore, the methods provided in the embodiments may be performed sequentially, synchronously or independently in accordance with another time sequences, not limited the time sequence described herein. Therefore, the implementation orders of the methods described in this specification are not to be construed as a limitation to the scope of the embodiments.

According to at least one of the above-mentioned embodiments, the processing load is reduced when the position of the subject which is the imaged object is changed.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fail within the scope and spirit of the inventions.

What is claimed is:

1. A medical imaging system, comprising:
    an ultrasonic probe configured to transmit and receive ultrasonic waves;
    positioning circuitry attached to the ultrasonic probe to detect a position of the ultrasonic probe;
    a memory to store a first mapping relationship between a first position of the ultrasonic probe when a subject is in a first position state and a second position of the ultrasonic probe when the subject is in a second position state, the first position and the second position being detected by the positioning circuitry;
    third mapping relationship estimation circuitry configured to estimate a third mapping relationship according to a registration deviation between an ultrasonic image formed by imaging a reference part of the subject when the subject is in the first position state and an ultrasonic image formed by imaging the reference part when the subject is in the second position state;
    repositioning circuitry configured to determine a target position of a volume image corresponding to the second position of the ultrasonic probe in the second position state according to the stored first mapping relationship, a second mapping relationship between the first position of the ultrasonic probe in the first position state and the target position of the volume image of the subject, and the third mapping relationship; and
    a display configured to obtain an image of the target position from the volume image according to the target position of the volume image determined by the repositioning circuitry, and display the obtained image,
    wherein a combination of the third mapping relationship and the first mapping relationship maps a third position of the ultrasonic probe to the first position so that the image formed by the ultrasonic probe at the first position for the subject in the first position state is the same as that imaged by the ultrasonic probe at the third position for the subject in the second position state.

2. The medical imaging system according to claim 1, wherein the third mapping relationship estimation circuitry is further configured to determine the registration deviation based on a variogram representing a local variance of values of pixels in the ultrasonic image.

3. The medical imaging system according to claim 1, wherein the reference part includes a part of the subject on which an influence of respiratory movement is below a predetermined level.

4. The medical imaging system according to claim 1, wherein the display is further configured to synchronously display the image of the target position and the ultrasonic image obtained by the ultrasonic probe.

5. The medical imaging system according to claim 1, wherein the second mapping relationship is obtained by registering the ultrasonic image of the subject in the first position state with the image of a corresponding position obtained from the volume image.

6. The medical imaging system according to claim 1, wherein the positioning circuitry comprises a magnetic positioning sensor fixed on the ultrasonic probe.

7. The medical imaging system according to claim 1, wherein the volume image includes at least one of a magnetic resonance image, a computed tomography image, and a positron emission tomography image.

8. The medical imaging system according to claim 1, further comprising:
    an ultrasonic imaging system, including the ultrasonic probe, configured to obtain a two-dimensional image, a three-dimensional image or a dynamic image.

9. A surgical guidance system, comprising:
    a medical imaging system, wherein the medical imaging system comprises
        an ultrasonic probe configured to transmit and receive ultrasonic waves;
        positioning circuitry attached to the ultrasonic probe to detect a position of the ultrasonic probe;
        a memory to store a first mapping relationship between a first position of the ultrasonic probe when a subject is in a first position state and a second position of the ultrasonic probe when the subject is in a second position state, the first position and the second position being detected by the positioning circuitry;
        third mapping relationship estimation circuitry configured to estimate a third mapping relationship according to a registration deviation between an ultrasonic image formed by imaging a reference part of the subject when the subject is in the first position state and an ultrasonic image formed by imaging the reference part when the subject is in the second position state;
        repositioning circuitry configured to determine a target position of a volume image corresponding to the second position of the ultrasonic probe in the second position state according to the stored first mapping relationship, a second mapping relationship between the first position of the ultrasonic probe in the first position state and the target position of the volume image of the subject, and the third mapping relationship; and
        a display configured to obtain an image of the target position from the volume image according to the target position of the volume image determined by the repositioning circuitry, and display the obtained image, wherein a combination of the third mapping relationship and the first mapping relationship maps a third position of the ultrasonic probe to the first position so that the image formed by the ultrasonic probe at the first position for the subject in the first position state is the same as that imaged by the ultrasonic probe at the third position for the subject in the second position state.

10. A medical imaging method, comprising:

detecting a first position of an ultrasonic probe that is configured to transmit and receive ultrasonic waves when a subject is in a first position state and detecting a second position of the ultrasonic probe when the subject is in a second position state;

estimating a third mapping relationship according to a registration deviation between an ultrasonic image formed by imaging a reference part of the subject when the subject is in the first position state and an ultrasonic image formed by imaging the reference part when the subject is in the second position state;

determining a target position of a volume image corresponding to the second position of the ultrasonic probe according to a first mapping relationship between the first position of the ultrasonic probe and the second position of the ultrasonic probe in the second position state, a second mapping relationship between the first position of the ultrasonic probe in the first position state and the target position of the volume image of the subject, and the third mapping relationship, the first mapping relationship being stored in a memory;

obtaining an image of the target position from the volume image according to the determined target position of the volume image; and displaying the obtained image, wherein a combination of the third mapping relationship and the first mapping relationship maps a third position of the ultrasonic probe to the first position so that the image formed by the ultrasonic probe at the first position for the subject in the first position state is the same as that imaged by the ultrasonic probe at the third position for the subject in the second position state.

* * * * *